United States Patent
Quillan et al.

(12) 
(10) Patent No.: US 6,602,856 B1
(45) Date of Patent: *Aug. 5, 2003

(54) ANTAGONISTS OF ALPHA-MELANOCYTE STIMULATING HORMONE AND METHODS BASED THEREON

(76) Inventors: J. Mark Quillan, 1624 Yale Station, New Haven, CT (US) 06526; Channa K. Jayawickreme, 2803 Bainbridge Dr., Durham, NC (US) 27713; Michael R. Lerner, 27 Jayne La., Hamden, CT (US) 06514

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/373,151

(22) Filed: Jan. 17, 1995

(51) Int. Cl.$^7$ .............................................. A61K 38/06
(52) U.S. Cl. ...................................... 514/18; 530/331
(58) Field of Search .......................... 530/331; 514/18

(56) References Cited

U.S. PATENT DOCUMENTS

| | | | |
|---|---|---|---|
| 4,305,872 A | 12/1981 | Johnston et al. | |
| 4,316,891 A | 2/1982 | Guillemin et al. | |
| 4,481,139 A | 11/1984 | Folkers et al. | 260/112.5 |
| 5,011,825 A | * 4/1991 | Konig et al. | 514/18 |
| 5,081,586 A | * 1/1992 | Barthel et al. | 364/497 |

FOREIGN PATENT DOCUMENTS

| | | | |
|---|---|---|---|
| DE | 3200273 | * | 10/1982 |
| EP | 162575 A2 | | 11/1985 |
| WO | WO 88/07551 | | 10/1988 |
| WO | WO 91/05563 | | 5/1991 |

OTHER PUBLICATIONS

Gao et al., Chem ABS #119:210398, 1993.*
Akamatsu et al., Chem ABS #117:131547, 1992.*
Sanyer et al, Peptide Research, vol. 2, No. 1 pp. 140–146, (1989).*
Sanyer et al., Peptide, vol. 11, pp. 351–357 (1989).*
Kawai et al., Chemical Abstract #114:221389, 1990.*
Dutta et al., 1986, J. Med. Chem. 29(7):1163–1171.
Tribbick et al., 1989, Mol. Immunol. 26(7):625–635.
Allen, Bennet M., 1916, "The Results of Extirpation of the Anterior Lobe of the Hypophysis and of the Larva of Rana Pipiens Larvae," *Science 44*: 755–758.
Arunlakshana et al., 1959, "Some Quantitative uses of Drug Antagonists" *British Journal of Pharmacology 14*: 48–58.
Cannon et al., 1986,"Melanocyte Stimulating Hormone Inhibits Immunostimulatory and inflammatory Actions of Interleukin 1", *The Journal of Immunology 137*: 2232–2236.
Chavin, 1956, "Pituitary–Adrenal Control of Melanization in Xanthicgoldfish, Carassius Auratus L. " *The Journal of Experimental Zoology 133*: 1–36.
Daniolos et al., 1990, "Action of Light on Frog Pigment Cells in Culture," *Pigment Cell Research 3*:38–43.
De Lean et al., 1978, "Simultaneous analysis of families of sigmoidal curves: application to bioassay, radioligand assay, and physiological dose–response curves" *American Journal of Physiology 235*: E97–E102.

(List continued on next page.)

*Primary Examiner*—Michael Borin
(74) *Attorney, Agent, or Firm*—Pennie & Edmonds LLP

(57) ABSTRACT

Peptide antagonists of α-melanocyte stimulating hormone are disclosed, together with methods of inhibiting the effects of α-melanocyte stimulating hormone on cells or tissues sensitive to that hormone. In particular, methods for lightening the pigmentation of skin and for treating malignant melanoma, as well as kits for practicing the invention are also disclosed.

10 Claims, 10 Drawing Sheets

OTHER PUBLICATIONS

Figure 2A:
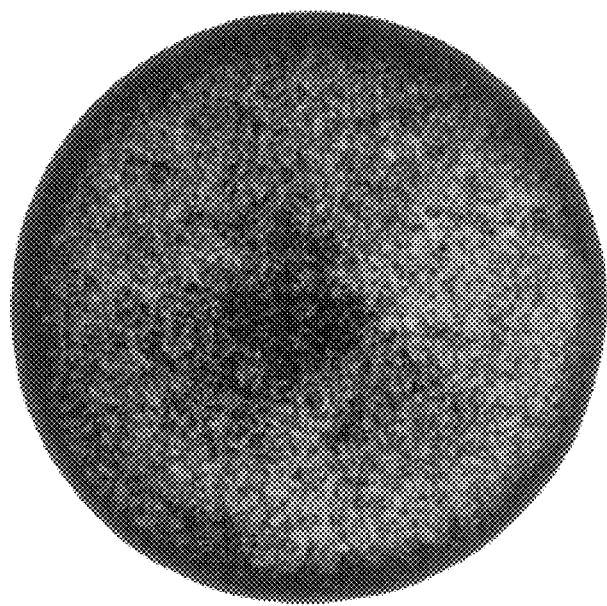

De Weid and Jolles, 1982, "Neuropeptides Derived From Pro–Opiocortin: Behavioral, Psychological, and Neurochemical Effects" *Physiological Reviews 62*: 976–1059.

De Weid et al., 1993, "Melanotropins as Neuropeptides", *Annals New York Academy of Sciences 680*: 20–28.

Felig et al., 1987, *Endocrinology and Metabolism* (McGraw Hill, New York, NY): pp. 1–26.

Graminski et al., 1993, "Pigment Dispersion in Frog Melanophores Can Be Induced by a Phorbol Ester or Stimulation of a Recombinant Receptor that Activates Phospholipase C", *The Journal of Biological Chemistry 268*: 5957–5964.

Halaban et al., 1993, "Pigmentation and Proliferation of Human Melanocytes and the Effects of Melanocyte–Stimulating Hormone and Ultraviolet B Light", *Annals New York Academy of Sciences 689*: 290–300.

Houghten et al., 1991, "Generation and use of synthetic peptide combinatorial libraries for basic research and drug discovery", *Nature 354*: 84–86.

Houghten et al., 1992, "The Use of Synthetic Peptide Combinatorial Libraries for the Identification of Bioactive Peptides", *BioTechniques 13*: 412–421.

Jayawickreme et al., 1994, Creation and functional screening of a multi–use peptide library, *Proceedings of the National Academy of Sciences 91*: 1614–1618.

Jayawickreme et al., 1994, "Discovery and Structure–Function Analysis of α–Melanocyte–Stimulating Hormone Antagonists" *The Journal of Biological Chemistry 269*: 29846–29854.

Karne et al., 1993, "Cloning and characterization of an Endothelin–3 Specific Receptor ($ET_c$ Receptor) from *Xenopus laevis* Dermal Melanophores", *The Journal of Biological Chemistry 268*: 19126–19133.

Lam et al., 1991, "A new type of synthetic peptide library for identifying ligand–binding activity", *Nature 354*: 82–84.

Lerner and McGuire, 1961, "Effect of Alpha–and Beta–Melanocyte Stimulating Hormones on The Skin Colour of Man", *Nature 189*: 176–179.

Luger et al., 1993, "Production of Immunosuppressing Melanotropins By Human Keratinocytes,"*Annals New York Academy of Sciences 680*: 567–570.

Marki et al., 1981, Total Solid–Phase Synthesis of Porcine Gut Gastrin Releasing Peptide (GRP), A Mammalian Bombesin, *Journal of the American Chemical Society 103*: 3178–3185.

McClintock et al., 1993, "Functional Expression of Recombinant G–Protein Coupled Receptors Monitored by Video Imaging of Pigment Movement in Melanophores" *Analytical Biochemistry 208*: 298–305.

Merrifield, 1963, "Solid Phase Peptide Synthesis. I. The Synthesis of a Tetrapeptide", *Journal of the American Chemical Society 85*: 2149–2154.

Mountjoy et al., 1992, "The Cloning of a Family of Genes That Encode the Melanocortin Receptors", *Science 257*: 1248–1251.

Murphy et al., 1983, "Antipyretic Potency of Centrally Administered α–Melanocyte Stimulating Hormone" *Science 221*: 192–193.

Potenza and Lerner, 1992, "A Rapid Quantitative Bioassay for Evaluating the Effects of Ligands Upon Receptors That Modulate cAMP Levels in a Melanophore Cell Line,"*Pigment Cell Research 5*: 372–378.

Potenza et al., 1992, "A Method for Evaluating the Effects of Ligands Upon $G_s$ Protein–Coupled Receptors Using a Recombinant Melanophore–Based Bioassay," *Analytical Biochemistry 206*: 315–322.

Potenza and Lerner, 1991, "A Recombinant Vaccinia Virus Infects Xenopus Melannophores," *Pigment Cell Research 4*: 186–192.

Rust, Charles Chapin, 1965, "Hormonal Control of Pelage Cycles in the Short Tailed Weasel (*Mustelaerminea bangsi*)" *General and Comparative Endocrinology 5*: 222–231.

Strand et al., 1993, "Melanotropins as Growth Factors", *Annals New York Academy of Sciences 680*: 29–49.

Tatro, 1990, "Melanotropin receptors in the brain are differentially distributed and recognize both corticotropin and α–melanocyte stimulating hormone", *Brain Research 536*: 124–132.

Vale et al., 1981, "Characterization of a 41–Residue Ovine Hypothalmic Peptide That Stimulates Secretion of Corticotrophin and β–Endorphin," *Science 213*: 1394–1397.

Varga et al., 1974, "Regulation of Melanocyte Stimulating Hormone Action at the Receptor Level: Discontinuous Binding of Hormone to Synchronized Mouse Melanoma Cells During the Cell Cycle," *Proceedings of the National Academy of Sciences 71*: 1590–1593.

Wu and Wu, 1987, "Receptor–mediated in Vitro Gene Transformation by a Soluble DNA Carrier System," *The Journal of Biological Chemistry 262*: 4429–4432.

\* cited by examiner

POSITION

| 1 | 2 | 3 |
|---|---|---|
| | AA$_1$ | AA$_1$ |
| | . | . |
| | . | . |
| | . | . |
| | AA$_{37}$ | AA$_{37}$ |
| Z$_{96}$ | Abu | Abu |
| | γ–Abu | γ–Abu |
| | ε–Ahx | ε–Ahx |
| | Aib | Aib |
| | β–Ala | β–Ala |
| | Hyp | Hyp |
| | Nle | Nle |
| | D–Nle | D–Nle |
| | Nva | Nva |
| | D–Nva | D–Nva |
| | Orn | Orn |

NH$_2$

FIG.1

| AA | R-GROUP | | IC$_{50}$ ($\mu$M) |
|---|---|---|---|
| Leu |  | P | 0.6 ± 0.2 |
| Nle |  | P | 0.9 ± 0.2 |
| Nva |  | P | 3.3 ± 1.1 |
| Met |  | P | 5.6 ± 2.6 |
| Ile |  | P | 49 ± 9 |
| Abu |  | P * | 82 ± 41 |
| Val |  | P | 237 ± 100 |
| Ala |  | P | INACTIVE |
| βAla | | P * | INACTIVE |

ANTAGONISTS OF ALPHA-MELANOCYTE STIMULATING HORMONE AND METHODS BASED THEREON

This invention was made with government support under grant no. N00014-91-J-1920 awarded by The Office of Naval Research. The government has certain rights in the invention.

1. INTRODUCTION

The present invention provides peptide antagonists of α-melanocyte stimulating hormone and methods of inhibiting the effects of α-melanocyte stimulating hormone on cells or tissues sensitive to that hormone, including lightening skin, modulating the immune response and treating malignant melanoma.

2. BACKGROUND OF THE INVENTION

Skin pigmentation and tanning are related to the amount and distribution of melanin in epidermal melanosomes. The epidermis cell population includes keratinocytes and the melanocytes that supply the keratinocytes with melanosomes, i.e., melanin containing pigment granules, via dendritic processes. Melanin is a dark pigment that is produced by the oxidation of tyrosine to dopa and dopaquinone by the enzyme tyrosinase, to produce compounds that polymerize to form melanin.

There are a number of localized hyperpigmentation disorders that presently lack any safe and effective method of cosmetic treatment. These include pigmented spots such as ephelides (freckles), solar lentigines (also called liver spots), acanthosis nigricans (a hypermelanotic disorder), cafe-au-lait spots, nevi (moles), and melasma (localized post-partum darkening of the skin). There is also a continuing interest and need for a method for regulating pigmentation tone for the total skin surface, either for cosmetic purposes, e.g., to lighten the complexion, or to block the deleterious effects on the appearance caused by certain endocrine disorders. Heretofore, no safe and effective method for achieving the regulation of epidermal pigmentation tone has been available.

The endogenous hormone that is implicated in the regulation of pigmentation is α-melanocyte stimulating hormone ("α-MSH") (Lerner et al., 1961, Nature 189, 176–179). α-MSH is also implicated in the regulation of central nervous system and immune system functions (De Weid, 1993, *Ann. NY Acad. Sci.* 680, 20–28; Tatro, 1990, *Brain Res.* 536, 124–132; Luger, et al.,1993, *Ann. N.Y. Acad. Sci.* 680, 567–570; Cannon, et al., 1986, *J. Immunol.* 137, 2232–2236; Murphy et 20 al., 1983, *Science* 221, 192–193), growth (Strand, F. l., et al., 1993, *Ann. NY Acad. Sci* 680, 29–49), mitogenesis (Halaban et al., 1993, *J. Ann. NY Acad. Sci.* 689, 290–300), and melanoma (Varga et al., 1974, *Proc. Natl. Acad. Sci. U.S.A.* 71, 1590–1593).

Indirect support for the hypothesis that α-MSH is an endogenous regulator of basal skin tone comes from experiments in which removal of the pituitary gland induces lightening of the pigmentation of fish, amphibians, and lower mammals (Chavin, 1956, *J. Exp. Zool.* 133, 1–36; Smith, 1916, *Science* 44, 75–758; Allen, 1916, *Science* 44, 755–758; Rust, C. C., 1965, *Gen. Comp. Endocrinol.* 5, 222–231).

In addition, anecdotal clinical reports claim that humans become abnormally pale as a consequence of the loss of pituitary function due to disease or hypophysectomy (Felig et al., 1987, *Endocrinology and Metabolism*, McGraw-Hill Book Company, New York, 1–26). In humans, MSH is released not only from the pituitary, but also apparently by dermal keratinocytes following exposure to ultraviolet light (Luger, et al., 1993, *Ann. N.Y. Acad. Sci.* 680, 567–570). While it is well known that injection of MSH into animals or humans causes an increase in skin tone beyond basal levels, the contribution of endogenous α-MSH to tonic baseline pigmentation has heretofore been unknown.

It has been shown that MSH effects an increase in tyrosinase activity of cultivated mouse melanoma cells. Synchronized cells were found to respond to MSH only in the G2 phase of the cell cycle. The binding of $^{125}$I-labeled MSH occurs predominantly in G2. Thus, it is proposed that MSH can activate melanoma cell adenylate cyclase by binding to an MSH receptor in the G2 phase (Varga et al., 1974, *Proc. Natl. Acad. Sci. U.S.A.*, 71(5), 1590–3).

Thus, a practical antagonist of α-MSH activity would provide a useful pharmacological agent for confirming the role of endogenous α-MSH, and provide for methods of regulating all of the biological functions mediated by α-MSH, including skin pigmentation tone and malignant melanoma cancer cells.

Recently, Jayawickreme et al., November 1994,*J. of Biol. Chem.* 269(47) 29846–29854, identified a series of polypeptide α-MSH antagonists, e.g., octapeptides and nonapeptides. However, larger peptide molecules have limited ability to penetrate tissues of interest. Therefore, there remains a need for a small molecule α-MSH antagonist, e.g., of less than 500 Da, better able to readily diffuse into tissue structures to regulate α-MSH sensitive tissues.

3. SUMMARY OF THE INVENTION

The present invention provides peptide antagonists of α-MSH and further provides methods for regulating the function of cells and tissues responsive to α-MSH hormone. The invention provides for peptide antagonists according to the active α-MSH peptides of table 1, infra. Thus, the invention provides for peptide antagonists of α-MSH comprising an amino acid sequence of R-S-T, wherein R, S and T are amino acid residues and R is selected from the group consisting of D-Trp, D-Phe, D-Tyr, Ac-D-Trp, Trp and D-His, except that when S is Arg and T is Nle or an amide thereof, then R is D-Phe, D-Tyr, Ac-D-Trp, Trp or D-His; when S is Lys, D-Arg, Leu, Nle, Ala, Met, or Abu, and T is Nle or an amide thereof, then R is D-Trp; and when S is Arg, and T is Leu, Nle, Nva, Met, D-Nle, Ile, Abu, Val, Arg or D-Arg or an amide thereof, then R is D-Trp; S is selected from the group consisting of Arg, Lys, D-Arg, Leu, Nle, Ala, Met, and Abu; and T is selected from the group consisting of Leu, Nle, Nva, Met, D-Nle, Ile, Abu, Val, Arg, D-Arg and amides thereof. The present invention also provides molecules having structures analogous to the disclosed peptide antagonists.

The invention also provides a method of inhibiting the activity of α-MSH in an α-MSH-responsive cell or tissue by contacting such a cell or tissue with a peptide antagonist of α-MSH according to the invention.

The invention further provides a method of lightening the skin complexion of an animal by administering an effective amount of a peptide antagonist of α-MSH according to the invention to an animal, e.g., a mammal such as a human, in need of such treatment. Methods of treatment are provided for pigmented spots, nevi, freckles, melasma and for local or systemic cosmetic lightening of the complexion. Administration may be topical or systemic.

The invention further provides a method of treating malignant melanoma by administering an effective amount of a peptide antagonist of α-MSH according to the invention to an animal e.g., a mammal such as a human in need of such treatment.

The invention further provides a method of modulating the immune system by administering an effective amount of a peptide antagonist of α-MSH according to the invention to an animal such as a human in need of such treatment.

In yet a further embodiment, the invention provides a pharmaceutical composition of a peptide antagonist according to the active α-MSH antagonist peptides of table 1, infra. Thus, the invention provides antagonists of α-MSH comprising an amino acid sequence of R-S-T, wherein R, S and T are amino acid residues and R is selected from the group consisting of D-Trp, D-Phe, D-Tyr, Ac-D-Trp, Trp and D-His, except that when S is Arg and T is Nle or an amide thereof, then R is D-Phe, D-Tyr, Ac-D-Trp, Trp or D-His; when S is Lys, D-Arg, Leu, Nle, Ala, Met, or Abu, and T is Nle or an amide thereof, then R is D-Trp; and when S is Arg, and T is Leu, Nle, Nva, Met, D-Nle, Ile, Abu, Val, Arg or D-Arg or an amide thereof, then R is D-Trp; S is selected from the group consisting of Arg, Lys, D-Arg, Leu, Nle, Ala, Met, and Abu; and T is selected from the group consisting of Leu, Nle, Nva, Met, D-Nle, Ile, Abu, Val, Arg, D-Arg or an amide thereof, together with a pharmaceutically acceptable carrier.

In an alternative embodiment, the invention provides a tripeptide antagonist of α-melanocyte stimulating hormone that is identified by the method of preparing a combinatorial screening library comprising a library of tripeptide molecules of random structure. The random combinatorial screening library is then contacted with a test system for α-melanocyte stimulating hormone activity, followed by identification of tripeptide molecules that antagonize the α-melanocyte stimulating hormone activity.

4. DESCRIPTION OF THE FIGURES

FIG. 1 illustrates the organization of the combinatorial library composed of 96 sub-libraries used for identification of the tripeptide antagonist. ABBREVIATIONS: Abu, 2-amino butyric acid; γ-Abu, 4-amino butyric acid; ε-Ahx, 6-amino hexanoic acid; Aib, 2-amino isobutyric acid; β-Ala, 3-amino propionic acid; Orn, ornithine; Hyp, trans hydroxyproline; Nle, norleucine; Nva, norvaline.

Figure 2B:
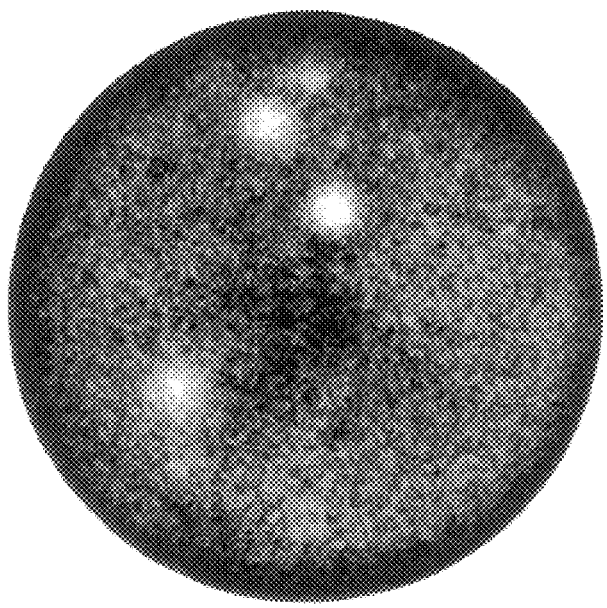

FIGS. 2A and 2B show video images of α-MSH antagonist responses, produced by beads from the combinatorial sub-library containing D-Trp at position 1 (i.e. D-Trp sub-library). The left image, (FIG. 2A), shows a 6-cm culture dish (Falcon) of agarose covered Xenopus melanophores, pretreated with melatonin (1 Nm for 30 min) and α-MSH (15 Nm for 2 min), just after application of approximately 600 beads from the D-Trp sub-library. By 60 min, (FIG. 2B), white circular patterns have appeared in response to local release from nearby beads.

Figure 3:
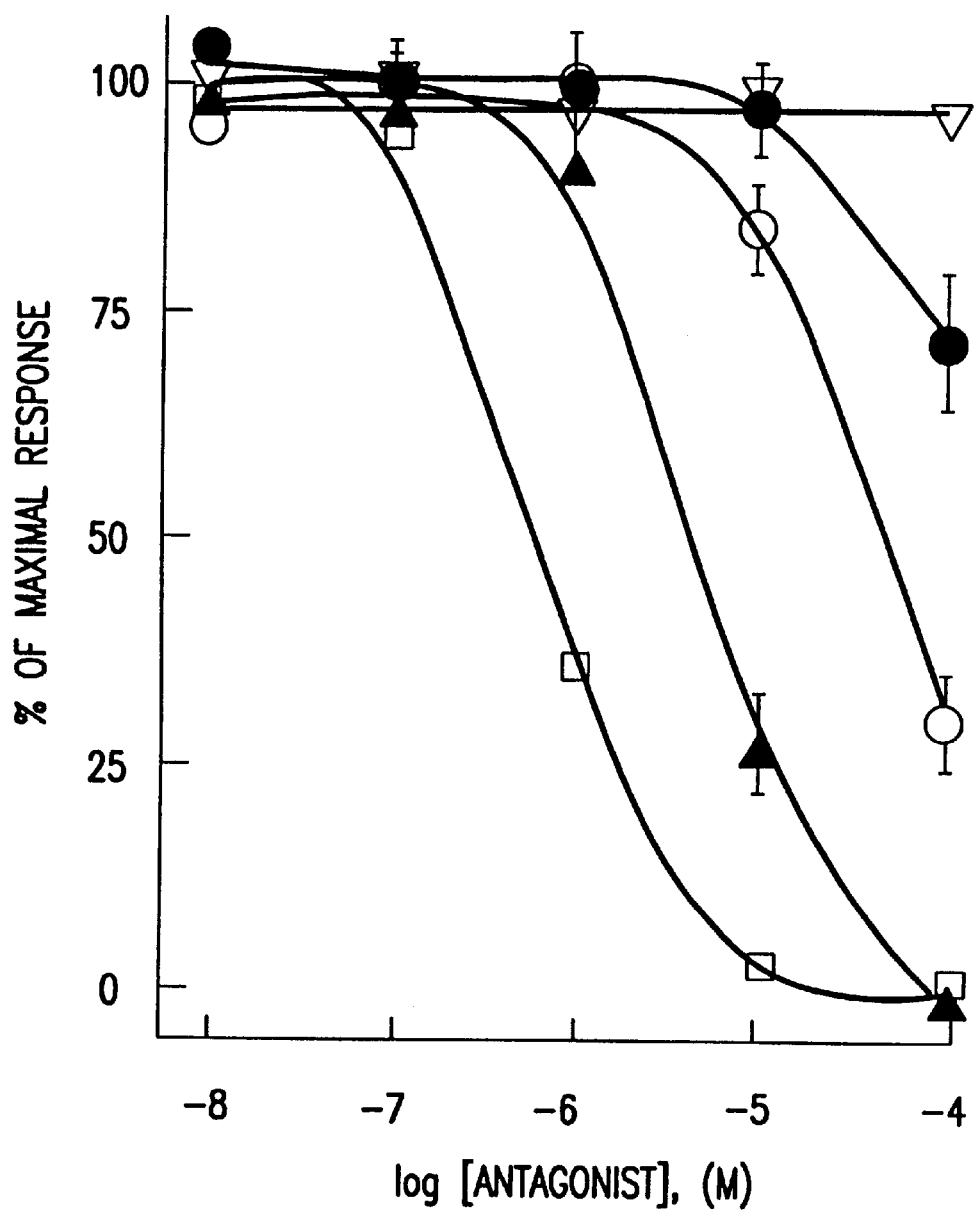

FIG. 3 provides a dose-response curve for candidate antagonists which were tested for their ability to inhibit α-MSH induced pigment dispersion in cultured Xenopus melanophore cells. The graph shows an example of inhibition curves for three peptides $A_1$ (square), $A_4$ (solid triangle), and $A_6$ (open circle) (see TABLE 1) identified from diffusion assays. Two other peptides not found in the library screens, $A_9$ (solid circle) and $A_{11}$ (open triangle), are included for comparison. Melanin dispersion responses were quantitated by measuring transmittance through a monolayer of cultured melanophores pretreated with 1 nM melatonin (Potenza, et. al., 1992, Anal Biochem. 206, 315–22) and curve fit with a logistic equation (De Lean et al., 1978, Am J. Physiol. 235, E97-E102). Each point represents the mean and sample standard deviation (SSD) of four independent measurements taken 2 hrs after addition of α-MSH (15 Nm) plus free-peptide at the indicated concentrations. Results are expressed as a percentage of relative treatment with α-MSH alone.

Figure 4:
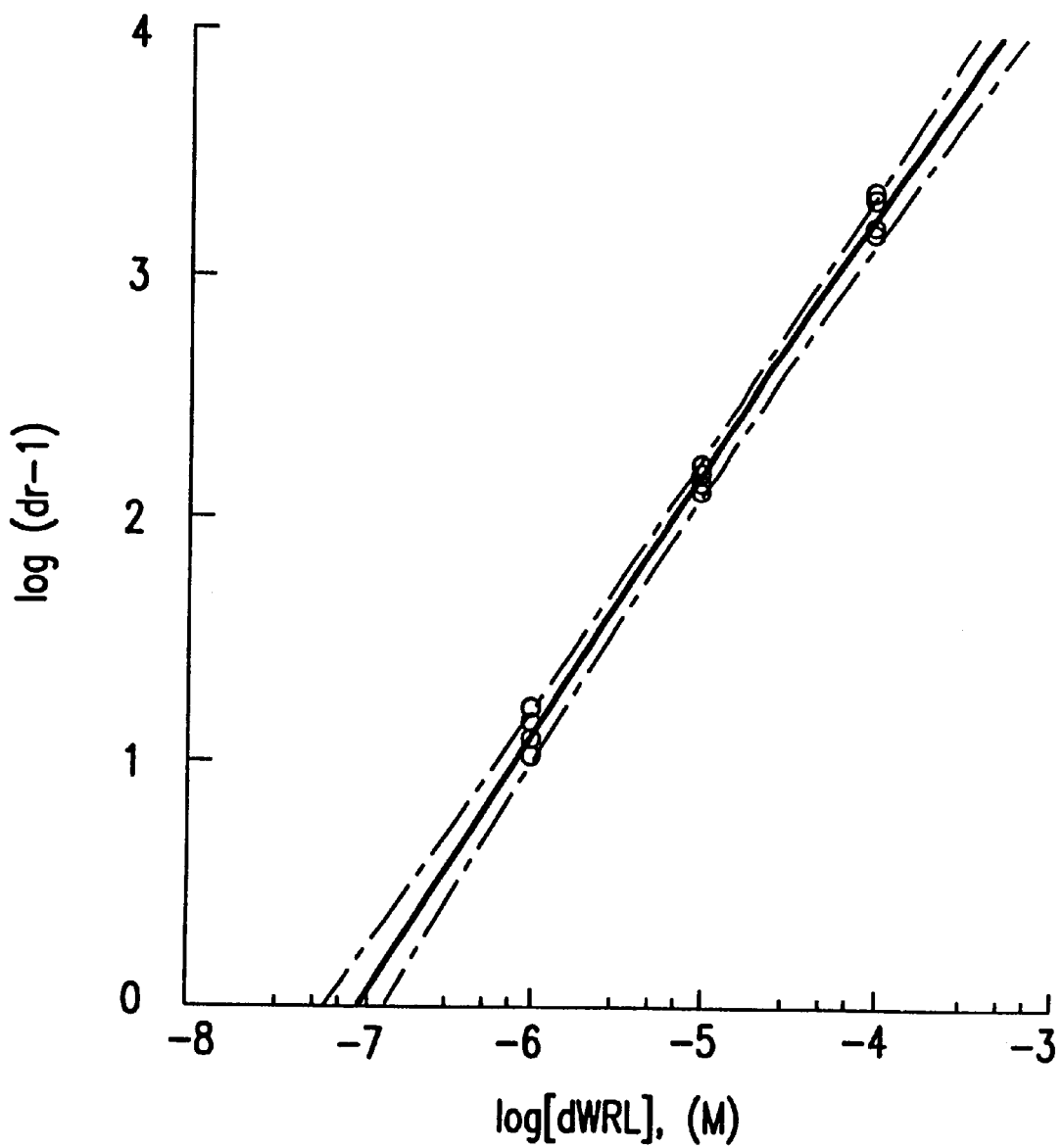

FIG. 4 illustrates competitive inhibition of α-MSH by D-Trp-Arg-Leu-NH$_2$ (dWRL) that is demonstrated using Schild regression analysis (Arunlakshana, et al., 1959, Br. J. Pharm. 14, 48–58). The equilibrium dissociation constant (pK$_c$) is 7.2±0.1 M, and the slope of the regression is 1.6±0.03. Broken lines indicate 99% confidence level.

Figure 5:
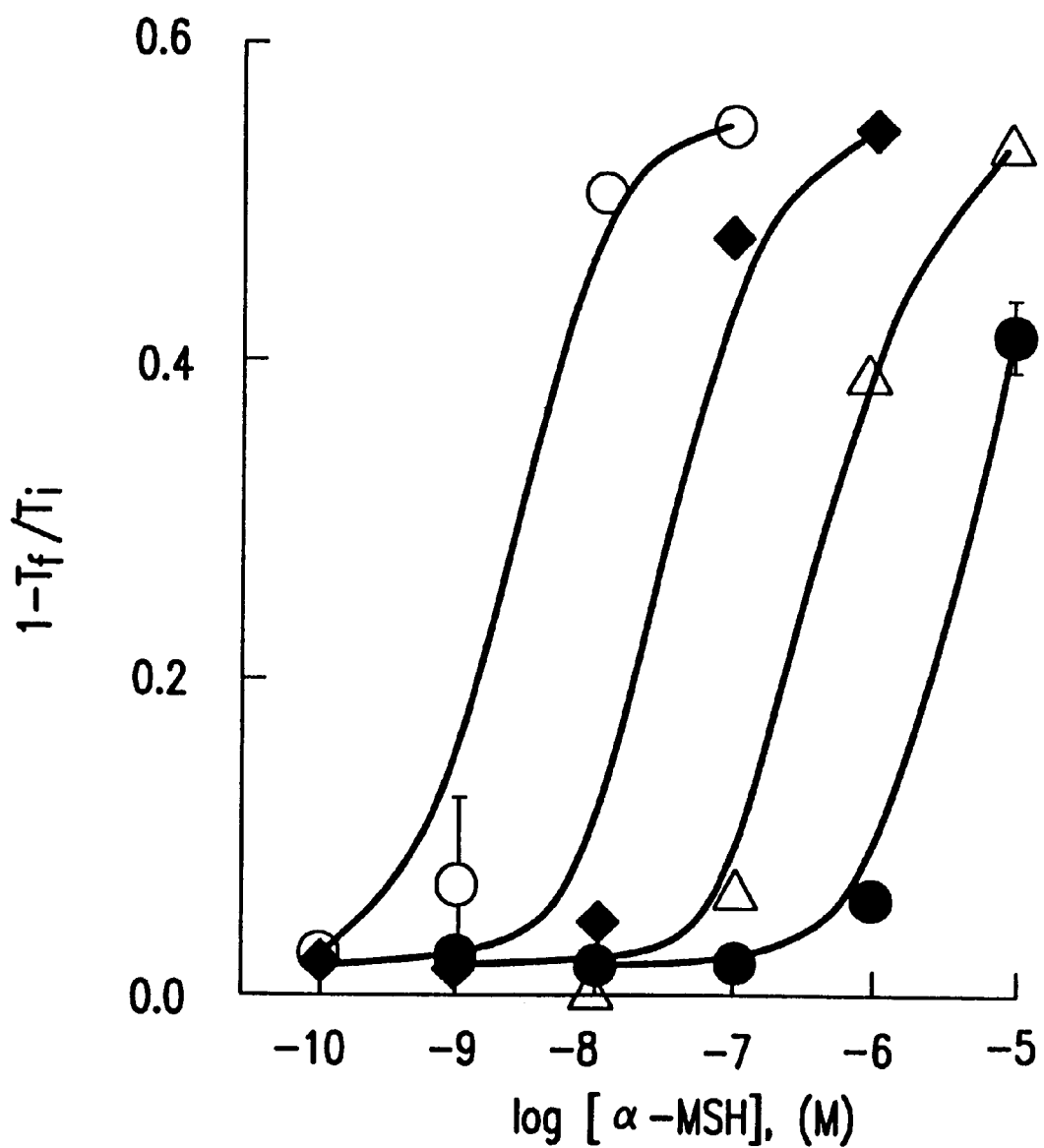

FIG. 5 illustrates the dose ratios (dr) for FIG. 4 that were obtained from concentration-response curves for α-MSH taken in the absence (open circles) and presence of 1 μM (solid diamonds), 10 μM (open triangles), and 100 μM (solid circles) DWRL. (EC$_{50}$ for α-MSH alone is 2.5±0.3 Nm, and for α-MSH+DWRL, 4.8±0.6 μM). Each point represents the mean and SSD of four independent transmittance measurements. Ti=initial transmittance (2 min.). Tf=final transmittance (60 min.). DWRL causes no change in EC$_{50}$ values for either vasoactive intestinal peptide ("VIP") or [Arg$^8$]-vasotocin ("AVT") (data not shown).

Figure 6:
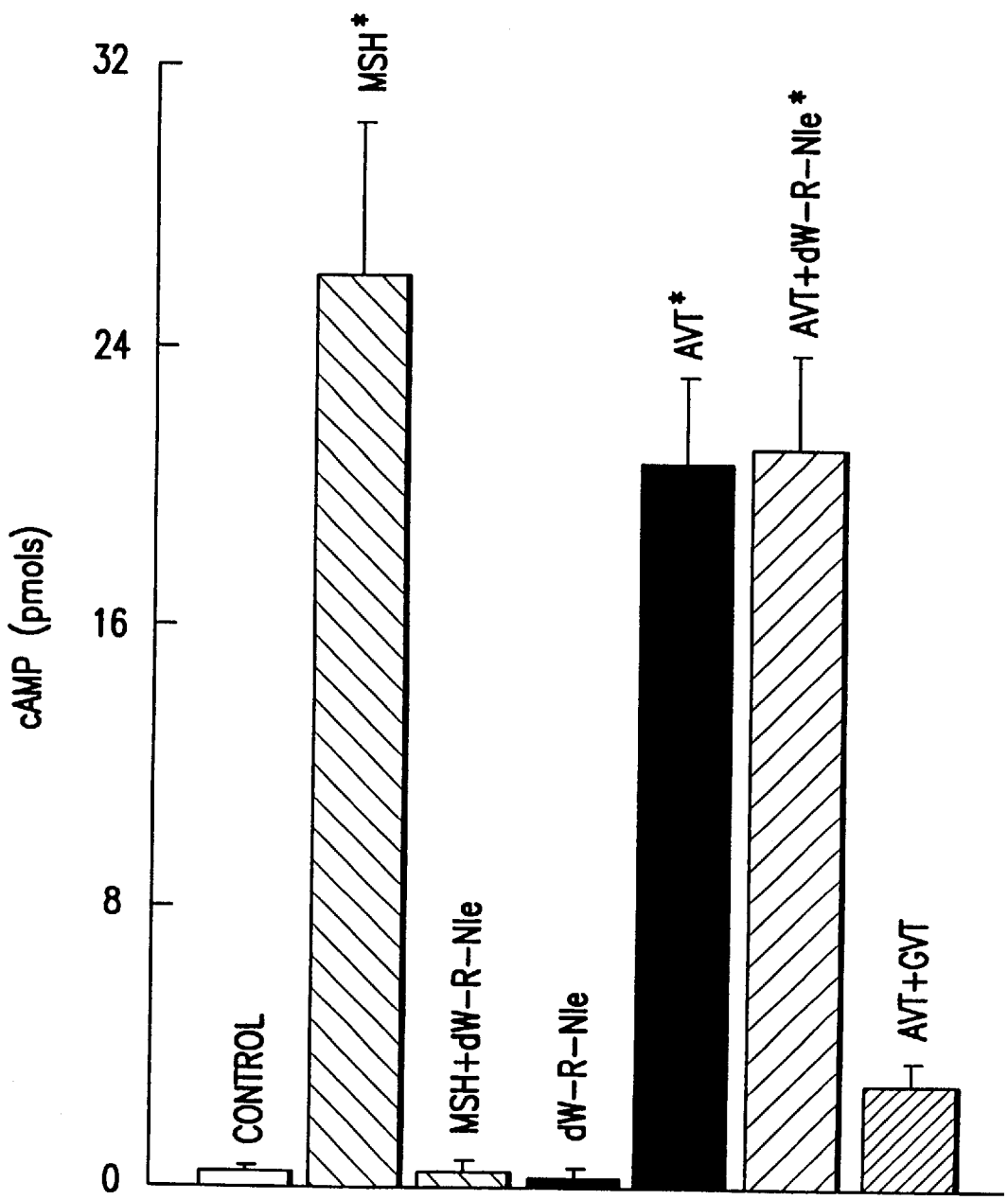

FIG. 6 illustrates that D-Trp-Arg-Nle-NH$_2$ (dW-R-Nle), at 40 μM, blocks α-MSH (10 Nm) mediated cAMP second messenger stimulation, but does not block cAMP stimulation evoked by AVT (8 nM). Oxytocin antagonist GVT ([d(CH$_2$)$_5$, Tyr (Me)$^2$, Orn$^8$]-Vasotocin; from Peninsula), at 20 μM, is used as a control to block responses evoked by 8 Nm AVT. Intracellular CAMP measurements were taken from confluent Xenopus melanophores grown in 24-well tissue culture plates (Falcon). Each bar represents the mean and SSD of four independent measurements. *(T-test; P<0.001) for all groups except those bearing asterisks.

Figure 7:
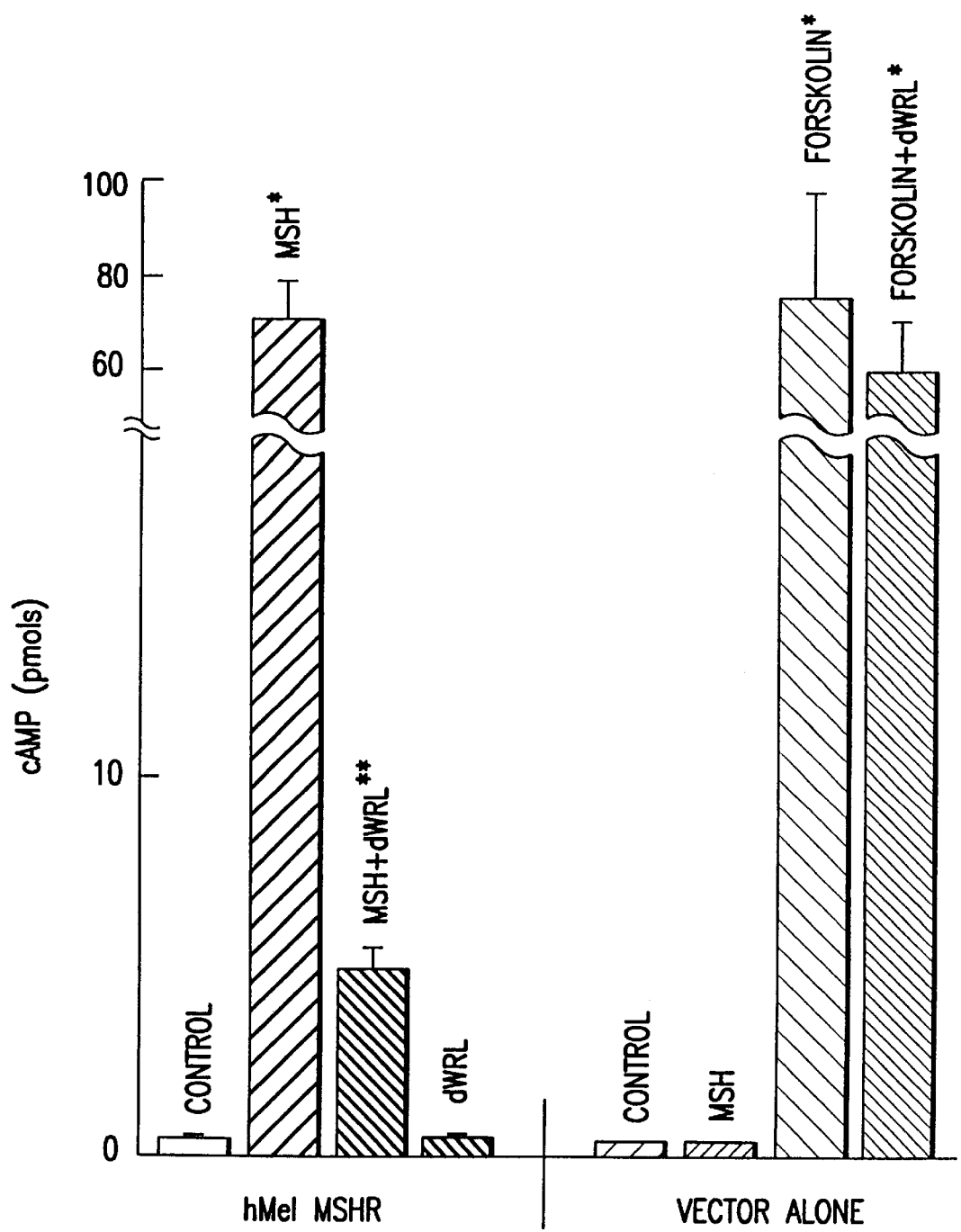

FIG. 7 shows the functional antagonism of a human MSH receptor by dWRL in Xenopus fibroblasts (Daniolos, et al., 1990, Pigment Cell Res 3, 38–43) transfected with "Vector alone" (pcDNAI/NEO, Invitrogen) or with "HMelMSHR" (pcDNAI/NEO) containing a human melanoma MSH receptor insert. Control=no additional drugs. MSH=5 nM α-MSH. dWRL concentration was 10 μM. Forskolin=100 μM forskolin (7β-desacetyl-7β-[g-(N-methylpiperazino)-butyryl; from Calbiochem).

Figure 8:

FIG. 8 is a photograph demonstrating that topical application of the tripeptide DWRL (1 Mm in H$_2$O) to the skin of Xenopus leavis causes a local lightening of pigmentation to "albino like" levels of a coloration.

Figure 9:

FIG. 9 is a photograph demonstrating that systemic injection of the tripeptide DWRL into Xenopus leavis causes a lightening of skin pigmentation on the entire body surface. Three animals were injected were injected with DWRL (40 μmols/kg) or with D-Trp-Abu-Arg-NH$_2$ (control), and within 20 minutes assumed the albino-like appearance as shown. The three control animals are dark.

Figure 10:
Figure 10:
Figure 10:
Figure 10:
Figure 10:
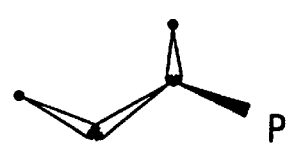
Figure 10:
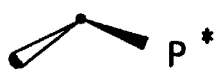
Figure 10:
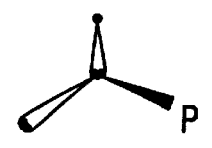
Figure 10:

FIG. 10 illustrates structure-function comparisons at the third position for the six most potent L-molecules identified by random screening from subpools containing D-Trp at position-1 and Arg at position-2. Three additional position-3 substitutions, not found in the random screen, are included for comparison. Antagonist activity correlates with hydrophobicity and charge characteristics of the R-group found at position 3. Chain length and stearic hindrance by β-carbon substitution are also important.

5. DETAILED DESCRIPTION OF THE INVENTION

The present invention relates to peptide antagonists according to the active α-MSH antagonist peptides of Table 1, infra. Thus, the invention provides antagonists of α-MSH and methods for regulating the function of cells and tissues responsive to α-MSH hormone. In particular, the present invention provides for peptide antagonists of α-MSH comprising an amino acid sequence of R-S-T, wherein R, S and T are amino acid residues and R is selected from the group consisting of D-Trp, D-Phe, D-Tyr, Ac-D-Trp, Trp and D-His, except that when S is Arg and T is Nle or an amide thereof, then R is D-Phe, D-Tyr, Ac-D-Trp, Trp or D-His; when S is Lys, D-Arg, Leu, Nle, Ala, Met, or Abu, and T is Nle or an amide thereof, then R is D-Trp; and when S is Arg, and T is Leu, Nle, Nva, Met, D-Nle, Ile, Abu, Val, Arg or D-Arg or an amide thereof, then R is D-Trp; S is selected from the group consisting of Arg, Lys, D-Arg, Leu, Nle, Ala, Met, and Abu; and T is selected from the group consisting of Leu, Nle, Nva, Met, D-Nle, Ile, Abu, Val, Arg, D-Arg and amides thereof. In a preferred embodiment, the peptide consists of more than ten amino acids, including but not limited to 15 amino acids. In other preferred embodiments, the peptide comprises no more than 8, or no more than 12, amino acid residues (including derivatives of amino acid residues or amino acid analogs).

In yet another preferred embodiment, the peptide comprises three contiguous amino acid residues as a tripeptide (including derivatives of amino acid residues or amino acid analogs), wherein the three amino acid residues are the active α-MSH antagonists as shown in Table 1, infra. The present invention also provides analogs and derivatives of the peptides.

The term "amino acid" or "amino acid residue" as used herein refers to naturally occurring, non-naturally occurring or derivatized amino acid residues or a molecule that has the conformation of an amino acid.

The term "peptide" refers to any molecule comprising a peptide bond consisting of naturally occurring, non-naturally occurring or derivatized amino acid residues or a molecule that has the conformation of an amino acid. A peptide bond as used herein refers to an amide bond linking two adjacent amino acid residues.

In a particular embodiment, the α-MSH antagonist is one of the following tripeptides: D-Trp-Arg-Leu; D-Trp-Arg-Nle; D-Trp-Arg-Nva; D-Trp-Arg-Met; D-Trp-Arg-D-Nle; D-Trp-Arg-Ile; D-Trp-Arg-Abu; D-Trp-Arg-Val; D-Trp-Arg-Arg; D-Trp-Arg-D-Arg; D-Trp-Lys-Nle; D-Trp-D-Arg-Nle; D-Trp-Leu-Nle; D-Trp-Nle-Nle; D-Trp-Ala-Nle; D-Trp-Met-Nle; D-Trp-Abu-Nle; D-Phe-Arg-Nle; D-Tyr-Arg-Nle; D-Ac-Trp-Arg-Nle; Trp-Arg-Nle and D-His-Arg-Nle. Compositions comprising one or more of the foregoing tripeptides are also provided.

In another embodiment, the peptide has a molecular weight of less than 500 Da.

In yet another embodiment, the peptide may be a tripeptide α-MSH antagonist identified by the screening of a random synthetic combinatorial library for α-MSH antagonist activity. Simply by way of example, the combinatorial library may be prepared according to the methods of Houghten et al., 1991, *Nature* 354, 84, Houghten et al., 1992, *Biotechniques* 13, 412 or Jayawickreme, et al., 1994, *Proc. Natl. Acad. Sci. U.S.A.* 91, 1614–1618, with the peptides synthesized in a structurally random fashion, unbiased towards homology with α-MSH. Randomness is defined so that the size and/or structure of a resulting peptide cannot be predicted at any position. It is also contemplated that other random libraries known to the art may be used to identify α-MSH antagonist peptides. Screening may be carried out by any methods known in the art, and in a preferred aspect, is carried out as described in the examples below.

The peptides and the amino acids comprising the peptides are not limited to the 20 naturally occurring amino acids. Non-classical amino acids include but are not limited to the D-isomers of the common amino acids, α-amino isobutyric acid, 4-aminobutyric acid, hydroxyproline, sarcosine, citrulline, cysteic acid, t-butylglycine, t-butylalanine, phenylglycine, cyclohexylalanine, β-alanine, designer amino acids such as β-methyl amino acids, Cα-methyl amino acids, Nα-methyl amino acids, and amino acid analogs in general. In addition, the amino acids can include Abu, 2-amino butyric acid; γ-Abu, 4-amino butyric acid; ε-Ahx, 6-amino hexanoic acid; Aib, 2-amino isobutyric acid; β-Ala, 3-amino propionic acid; Orn, ornithine; Hyp, trans hydroxyproline; Nle, norleucine; Nva, norvaline. Furthermore, the amino acid can be D (dextrorotary) or L (levorotary). Furthermore, the peptides and/or the amino acids can be derivatized by blocking groups, including but not limited to, acetylation, or carboxylation at the amino-terminus and amidation at the carboxy-terminus to provide protected derivatives.

The α-MSH antagonist peptides identified by combinatorial screening may be prepared by methods that are known in the art. For example, in brief, solid phase peptide synthesis consists of coupling the carboxyl group of the C-terminal amino acid to a resin and successively adding N-alpha protected amino acids. The protecting groups may be any known in the art. Before each new amino acid is added to the growing chain, the protecting group of the previous amino acid added to the chain is removed. The coupling of amino acids to appropriate resins is described by Rivier et al., U.S. Pat. No. 4,244,946. Such solid phase syntheses have been described, for example, by Merrifield, 1964, *J. Am. Chem. Soc.* 85:2149; Vale et al. 1981, *Science* 213:1394–1397; Marki et al., 1981 *J. Am. Chem. Soc.* 103:3178 and in U.S. Pat. Nos. 4,305,872 and 4,316,891. In a preferred aspect, an automated peptide synthesizer is employed.

Purification of the synthesized peptides can be carried out by standard methods including chromatography (e.g., ion exchange, affinity, and sizing column chromatography), centrifugation, differential solubility, or by any other standard technique for the purification of proteins. In a preferred embodiment, reverse phase HPLC (high performance liquid chromatography) is employed.

Structure-function relationships determined from the tripeptide antagonists disclosed herein, as discussed infra, and as shown by FIG. 10 for the third amino acid position, may also be used to prepare analogous molecular structures also having α-MSH inhibitory properties. Thus, the invention is contemplated to include molecules in addition to those expressly disclosed that share the structure, hydrophobicity, charge characteristics and side chain properties of the peptide antagonists exemplified herein.

5.1 α-MSH Antagonists have Therapeutic and Cosmetic Utility

α-MSH peptide antagonists have therapeutic and cosmetic utility in the modulation of functions mediated by α-MSH, for example, the lightening of the pigmentation of skin, the modulation of the immune system and the treatment of melanoma.

By "lightening" is meant the reduction of pigment tone provided by melanin present in the skin to provide a lighter skin complexion. While not wishing to be bound by any particular mechanism of action, it is believed that the peptide antagonists are competitive inhibitors of α-MSH at α-MSH receptors, resulting in a blockade of the pigmentation maintaining effects of endogenous α-MSH. Thus, the melanin particles present in α-MSH-responsive cells disperse in the presence of the α-MSH antagonist peptide due to blockade of the endogenous α-MSH receptor. This results in the removal of the MSH tonic effect on melanin aggregation. When the peptides are administered topically, the skin lightens where the peptide is applied. When the peptide is administered systemically, the entire skin surface may become significantly lighter in pigmentation tone.

The α-MSH antagonist peptides may be used to treat the following localized conditions including, but not limited to, pigmented spots or areas such as nevi or moles, freckles, melasma and postinflammatory hyperpigmentation. The complexion may also be lightened for cosmetic purposes both locally and systemically, as desired.

The α-MSH antagonist peptides provide methods for treating malignant melanoma by administration to a subject of an effective amount of a peptide antagonist according to the invention.

The invention also provides for methods for modulating the immune response of an animal or person by administration of an effective amount of a peptide antagonist of α-MSH to an animal or person in need of such treatment.

In addition, other diseases and clinical correlates of undesirable α-MSH activity can be treated with α-MSH antagonist peptides according to the invention.

5.2 Identification of Peptide Antagonists of α-MSH

Traditional approaches to drug development for peptide receptors are often based on the screening of altered native agonist peptide structures and generally leads to the identification of large molecules. In contrast, as described in the examples, the small molecule peptide antagonists of α-MSH according to the invention were identified by an alternative strategy of screening large numbers of random small tripeptide molecules prepared on bead surfaces in a multi-use combinatorial peptide library ("MUPL") according to the diffusion assay of Jayawickreme, et al., 1994, *J. Biol. Chem.* 269, 29846–29854 ("Jayawickreme I") and Jayawickreme et al., 1994 *Proc. Natl. Acad. Sci (U.S.A.)* 91, 1614–1618 ("Jayawickreme II") incorporated herein by reference in their entireties.

As described in the specific examples, the employed method allowed the screening of a library of beads bearing random tripeptide molecules. The bioassay medium consisted of melanophores on agarose gel pretreated with melatonin. The beads were then contacted with the agarose gel. Controlled release of peptides from the beads was accomplished by a gas-phase release procedure according to Jayawickreme I and II, supra. Pigment dispersion induced by diffusion of released peptides was observed within 5 or 10 minutes, and was monitored by video image subtraction.

5.3 Treatment and Compositions

The invention provides methods of treatment by administration to a subject of an effective amount of an α-MSH antagonist peptide according to the invention. In a preferred aspect, the peptide is purified. The subject is preferably an animal, e.g., a mammal, and most preferably a human.

Various delivery systems are known and can be used to administer the α-MSH antagonist peptide of the invention, e.g, aqueous solution, encapsulation in liposomes, microparticles, microcapsules, receptor-mediated endocytosis (see, e.g., Wu and Wu, 1987, *J. Biol. Chem.* 262, 4429–4432). Methods of administration include but are not limited to direct application to the skin, intradermal, intramuscular, intravenous, intranasal, epidural and oral routes. The peptides according to the invention may be administered by any convenient route, for example, by infusion or bolus injection, by absorption through epithelial or mucocutaneous linings (e.g., oral mucosa, rectal and intestinal mucosa).

In a specific embodiment, it may be desirable to administer the peptide according to the invention locally to the area it is desired to treat by any of the above described methods.

The present invention also provides pharmaceutical compositions. Such compositions comprise a therapeutically or cosmetically effective amount of a peptide according to the invention, and a pharmaceutically acceptable carrier or excipient. Such a carrier includes but is not limited to water, saline solution, e.g., physiological saline, buffered saline, dextrose, glycerol, ethanol, and combinations thereof. The formulation should suit the method of administration.

The composition, if desired, can also contain minor amounts of wetting or emulsifying agents, or pH buffering agents. The composition can be a liquid solution, suspension, emulsion, tablet, pill, capsule, sustained release formulation, cream, gel or powder. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate.

In a specific embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the compositions is administered by injection, an ampoule of sterile water for injection or saline can be provided so that the ingredients may be mixed prior to administration.

The peptide of α-MSH antagonists of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the peptide α-MSH antagonist of the invention which will be effective in the treatment of a particular disorder or cosmetic condition will depend on the antagonist nature of the disorder or condition, and can be determined by standard clinical techniques. In addition, in vitro or in vivo assays may optionally be employed to help identify optimal dosage ranges. The precise dose to be employed in the formulation will also depend on the route of administration, and the seriousness of the disease or cosmetic condition and should be decided according to the judgment of the practitioner and each patient's circumstances. Effective doses may be extrapolated from dose-response curves derived from in vitro or animal model test systems as provided herein.

An effective amount of the peptide antagonists of α-MSH is readily determined by administering graded doses of peptide antagonists according to the invention and observing the desired effect. The data provided in Table 1, and in FIGS. 2–9, infra, will assist in determining the effective amounts necessary for the purpose of skin lightening by providing $IC_{50}$ concentrations, dose-response curves for representative peptides and in vivo examples.

In one embodiment, the effective concentration for dWRL (D-Trp-Arg-Leu) in a topical formulation for, e.g., skin lightening, is in the range of 1 μM through 10 mM. In a preferred embodiment, the effective concentration of dWRL for a topical formulation is in the range of 100 μM through 5 mM. In a more preferred embodiment, the effective concentration for a topical formulation is in the range of 500 μM through 2 mM. In a particular embodiment, the effective concentration for a topical formulation is about 1 mM.

In another embodiment, an effective dose of dWRL for systemic administration for, e.g., the lightening of skin, is in the range of 1 through 4000 μmol/kg of body weight. In a preferred embodiment, the effective dose of dWRL for systemic administration for, e.g., the lightening of skin, is in the range of 20 through 200 μmol/kg of body weight. In a more preferred embodiment, the effective dose of dWRL for systemic administration for, e.g., the lightening of skin, is in the range of 30 through 100 μmol/kg of body weight. In another embodiment, the effective dose of dWRL for systemic administration is in the range of 30 through 100 μmol/kg of body weight.

The effective concentrations and doses for each of the other exemplified tripeptide antagonists may, for example, be readily determined by reference to the $IC_{50}$ Table 1 showing the relative potencies of the peptide antagonists to the dWRL tripeptide.

In another alternative embodiment, the invention comprises kits containing an effective amount of an α-MSH antagonist peptide according to the invention. Thus, the kit is contemplated to comprise one or more containers containing at least one α-MSH antagonistic peptide according to the invention. Simply by way of example, the kit will contain α-MSH antagonist peptide or peptides formulated for application to the skin, or for administration by intradermal, intramuscular, intravenous, intranasal, epidural and oral routes of administration. The kits may contain a liquid solution, suspension, emulsion, tablet, pill, capsule, sustained release formulation, cream, gel or powder form of the α-MSH antagonist peptide in premixed form or as separate ingredients ready to be mixed or formulated into a peptide formulation or a pharmaceutical composition, comprising an effective amount of an α-MSH antagonist peptide according to the invention.

The invention is further described in the following examples which are in no way intended to limit the scope of the invention.

6. EXAMPLES

6.1 Design and Construction of the Tripeptide Combinatorial Library

A synthetic tripeptide random combinatorial library was prepared using Fmoc (fluorenylmethoxycarbonyl) chemistry on MBHA (4-methyl-benzhydrylamine) linked resin (substitution level 0.95 mmol/g) as described by Jayawickreme I and II, supra, in combination with simultaneous multiple peptide synthesis (Lam et al., 1991, Nature 354, 83–84 and Houghten et al, Nature 354, 84–86). A divide, couple and recombine process was used to synthesize the tripeptides on sublibraries of beads.

Each sub-library contained 2304 (1×48×48) possible tripeptide or tripeptide-like sequence combinations. $Z_{96}$ (see FIG. 1) was used to represent the position 1 molecule that comprises each sub-library. Position 1 contains one of the 48 molecules listed for the other 2 positions, or one of 48 acetylated (Ac) equivalents. $AA_1$ to $AA_{37}$ at position 2 and 3 are the 20 standard levorotatory (not prefixed) amino acids, minus Cys, plus 18 equivalent dextrorotary (D) isoforms. Eleven additional molecules as listed bring the total to 48.

In preparation for screening, approximately 4% of total bead-attached molecules were released using the controlled gas-phase trifluoroacetic acid (TFA) cleavage procedure, followed by treatment with gaseous $NH_3/H_2O$ to render the beads non-toxic for direct use in biological assays. Detached molecules remain non-covalently associated with their beads of origin until released for assay.

6.2 Functional Biossay

Xenopus laevis dermal melanophores were maintained in cell cultures as described previously (Daniolos et al; 1990, Pigment Cell Res. 3, 38–43; Potenza et al; 1991, Pigment Cell Res. 4, 186–192 and Karne et al; 1993, J. Biol. Chem. 268, 19126–19133). 1.5 million cells were seeded into 6-cm tissue culture dishes (Falcon) in 5 ml of fibroblast-conditioned media and incubated at 27° C. for at least 48 h. For each assay, the media was removed from the dish and replaced with 3.5 ml of 0.9% Sea Plaque Agarose. The cells were pretreated with melatonin (1 nM for 30 min) and α-MSH (15 nM for 2 min), and approximately 600 beads from each sublibrary were applied. Beads remained separated from the melanophore cell layer by an intervening 2-mm thickness of agarose, allowing only dissociated free molecules to interact at the cell surface.

Pigment translocation (dispersion) induced by tripeptide was monitored by video image substraction as described by McClintock et al., 1993, Anal. Biochem. 209, 298–305.

6.3 Peptide Sequencing

Peptide beads were selected from positive areas, washed with N-methylpyrrolidoire ("NMP"), dichloromethane ("DCM") and methanol ("MeOH") and reprepared for a second round of screening for selecting single beads responsible for positive signals by sparsely distributing the beads on a polyethylene sheet. Beads selected from the first round of screening were recleaved by the gaseous trifluoroacetic acid/NH3/H2O procedure. Single beads responsible for positive signals were then collected, washed with NMP, DCM and MeOH, placed on a glass fiber filter and sequenced using an Applied Biosystems 476A sequencer.

6.4 Dose-Response Studies

For dose-response studies all tripeptides were synthesized on Rink Amide MBHA resin 0.25 mmol scale using standard Fmoc chemistry. After synthesis, peptides were purified suing HPLC and reverse-phase chromatography on a C18 column. The dose-response curves were obtained by microtiter plate assays (Potenza et al, 1992, Pigment Cell Res. 5, 372–378). Melanophore cells (18,000/well) were plated on 96-well tissue culture plates (Falcon). Before an assay, the media was supplemented with fibroblast-conditioned media containing 1 nm α-MSH, 1 nm melatonin and varying concentrations of tripeptide. For control experiments, 1 nm α-MSH was replaced with bombesin-[8–14] fragment, oxytocin, or no α-MSH. Dose-response curves or competitive inhibition curves for α-MSH were obtained by varying the concentration of α-MSH at different concentrations of tripeptides.

6.5 Results

Screening of the multi-use peptide library as described above was performed at the 10 picomole release level per bead (4% of the total) so that responses from molecules with potencies as low as 100 μM could be observed. The 221,184 component library was organized as 96 sub-libraries with 2,304 different peptide combinations per pool, each defined by the chemical structure of the amino terminal position. The sub-libraries beginning with D-Trp, D-Phe, D-Tyr, and Ac-D-Trp produced response patterns indicating the presence of multiple antagonist-like molecules, with the most numerous and potent signals being elicited by beads from the D-Trp sub-library (FIG. 4). Similar signals were not observed from any of these sub-libraries when pigment dispersion was activated with 8 nM AVT ($[Arg^8]$-vasotocin from Sigma; $EC_{50} \approx 2$ nM) or 4 nM VIP (Vasoactive Intestinal Peptide from Sigma; $EC_{50} \approx 1$ nM) in place of 15 nM α-MSH (Peninsula; $EC_{50} \approx 2$ nM).

After identification by the diffusion assay, candidate antagonists were resynthesized, purified (Jayawickreme I and II, supra) and tested (FIGS. 2–9). The results are organized and tabulated by TABLE 1, below. The two most potent antagonists, D-Trp-Arg-Leu-$NH_2$ (DWRL) and D-Trp-Arg-Nle-$NH_2$ have $IC_{50}$ values of 620±150 nm (mean±SE) and 930±220 Nm respectively, against 15 Nm α-MSH. These antagonists are competitive and specifically block α-MSH induced activation of endogenous amphibian and transfected human MSH-receptors (FIGS. 2–9). The tripeptide DWRL has an equilibrium dissociation constant (Ke) of 63±15 Nm (FIG. 2c), in line with a predicted $IC_{50}$ of approximately 96 Nm had α-MSH been applied at its $EC_{50}$ value.

TABLE 1

| | PEPTIDE SEQUENCE | | | |
| --- | --- | --- | --- | --- |
| A | D-Trp | —Arg | —X | —$NH_2$ | $IC_{50}$ (μM) |
| $A_1$ | | | Leu | | 0.62 ± 0.15 |
| $A_2$ | | | Nle | | 0.93 ± 0.22 |
| $A_3$ | | | Nva | | 3.3 ± 1.1 |
| $A_4$ | | | Met | | 5.6 ± 2.6 |
| $A_5$ | | | D-Nle | | 9.9 ± 1.8 |
| $A_6$ | | | Ile | | 49 ± 9 |
| $A_7$ | | | Abu | | 82 ± 41 |
| $A_8$ | | | Val | | 237 ± 100 |
| $A_9$ | | | Arg | | 261 ± 68 |
| $A_{10}$ | | | D-Arg | | 664 ± 397 |
| $A_{11}$ | | | γAbu | | Inactive |
| $A_{12}$ | | | εAhx | | Inactive |
| $A_{13}$ | | | Ala | | Inactive |
| $A_{14}$ | | | βAla | | Inactive |
| B | D-Trp | —X | —Nle | —$NH_2$ | |
| $B_1$ | | Lys | | | 15 ± 1 |
| $B_2$ | | D-Arg | | | 30 ± 11 |
| $B_3$ | | Leu | | | 48 ± 2.2 |
| $B_4$ | | Nle | | | 59 ± 12 |
| $B_5$ | | Ala | | | 65 ± 18 |
| $B_6$ | | Met | | | 121 ± 27 |
| $B_7$ | | Abu | | | 405 ± 69 |
| $B_8$ | | Asp | | | Inactive |
| C | X | —Arg | —Nle | —$NH_2$ | |
| $C_1$ | D-Phe | | | | 4.4 ± 1.2 |
| $C_2$ | D-Tyr | | | | 28 ± 2 |
| $C_3$ | Ac-D-Trp | | | | 43 ± 8 |
| $C_4$ | Trp | | | | 100 ± 2 |
| $C_5$ | D-His | | | | 318 ± 105 |

6.6 Structure-Function Relationships

In addition to identifying tripeptide antagonists with molecular weights of less than 500 daltons which are readily able to provide systemic and topical methods of blocking endogenous α-MSH activity, the simultaneous detection of multiple antagonist signals arising from various sub-libraries provided an opportunity to compare similarities and differences in antagonist structure. This allowed determinations of components that contribute to receptor interaction and blockade, and the information is potentially useful for further development of non peptide antagonists. Active sequences were deduced iteratively by the screening sub-pools of the D-Trp sub-library.

For example, diffusion assay response patterns indicated that the most potent molecules contain Arg at position 2, while other position 2 subpools (i.e., Lys, D-Arg, Met, Leu and Nle) displayed lesser degrees of MSH-receptor antagonist-like activity. TABLE 1, A1 to A6, shows the six most potent molecules identified by screening the D-Trp-Arg-X subpool.

After identification by the diffusion assay, candidate antagonists were resynthesized, purified (Jayawickreme I and II supra) and tested (FIGS. 2–9). The two most potent antagonists, D-Trp-Arg-Leu-$NH_2$ (dWRL) and D-Trp-Arg-Nle-$NH_2$ have $IC_{50}$ values of 620±150 nM (mean±SE) and 930±220 nM respectively, against 15 nM α-MSH. These antagonists are competitive and specifically block α-MSH induced activation of endogenous amphibian and transfected human melanoma MSH-receptors (FIGS. 7–9). The peptide dWRL has an equilibrium dissociation constant (Ke) of 63±15 nM (FIG. 5), in line with a predicted $IC_{50}$ of approximately 96 nM had α-MSH been applied at its $EC_{50}$ value.

The multiple MSH-receptor antagonist molecules identified from the D-Trp-Arg-X subpool comprises a set of structurally related peptides (FIG. 10) which form a set of permissible substitutions, wherein activity is not abolished by differences in structure at position 3. Within this group, IC (inhibitory concentration) measurements reveal that antagonist potency is positively correlated with the length of the hydrocarbon side-chain group, i.e., Nle>Nva>Abu>Ala, and negatively correlated with the presence of a β-methyl group, i.e., Nva>Ile and Abu>Val. Removal of the γ-methyl group from Leu results in a 50% decrease in antagonist potency as evidenced by comparison to Nva. When Met is located at position 3, there is a 6-fold reduction in potency compared to Nle, which has a similar but non-sulfur containing R-group. The strongest hydrophilic, charged substitution tested, Arg, causes a 300-fold decrease in potency compared to Nle (see TABLE 1, A). D-isomer subpools also contained positive signals, but has reduced potency compared to L-isomer subpools. D-Nle, included for comparison, was ten-fold more potent than the L-isomer at the third position.

The vast majority of tripeptides screened with the diffusion assay showed no α-MSH antagonist-like activity. Although this is expected given the high specificity of receptor-ligand interactions, negative results are informative. The lack of activity in most library pools tested, suggests that changes made to position 1 are not well tolerated in terms of receptor interaction. Besides D-Trp, only the clearly related D-Phe, and to a lesser extent D-Tyr, in the non-acetylated pools were found to display significant α-MSH antagonist-like activity. Confirmation of this observation comes from the finding that they are also the two most potent permissible position 1 substitutions in a general X-Arg-Nle-NH$_2$ structure (see TABLE 1, C1 and C2), where X represents all 48 non-acetylated combinations described in FIG. 1.

Thus, positive signals observed in screening subpools probably arise as a result of structural similarity to positives in the D-Trp library and do not represent additional unrelated structures. A similar picture apparently holds for positives observed within the D-Trp library position subpools. Substitutions of X in the D-Trp-X-Nle-NH$_2$ structure with Lys, D-Arg, Met, Leu, and Nle, result in peptides which display antagonist activity (see TABLE 1, B1 to B5), and, as expected, each has a potency less than with Arg at position 2. Therefore, it appears that peptides selected from random screens because they give the strongest signals, are in fact the most potent MSH-receptor antagonists present in the library. Variations in the combinatorial assay, bead size for example, contribute less to differences in signal strength than does a one or two order difference in potency.

6.7 Cyclic AMP Quantitation

Melanophores were plated confluently into 24-well tissue culture (Falcon) plates two days before the assay. Immediately prior to an assay, cells were washed with 70% L-15 medium (Sigma) containing 0.05% bovine serum albumin and then treated with 1 nm melatonin in the same medium. Then, cells were washed for 5 min in 70% L-15+0.05% bovine serum albumin+0.5 mm 3-isobutyl-1-methylxanthine (Aldrich)+1 nm melatonin, followed by 30 min of treatment with the test drug in the same media. After the drug treatment, cells were washed twice with 70% phosphate-buffered saline.

As shown by FIG. 6, D-Trp-Arg-Nle-NH$_2$ (dW-R-Nle), at 40 μM, blocks α-MSH (10 nM) mediated cAMP second messenger stimulation, but does not block cAMP stimulation evoked by AVT (8 nM). Oxytocin antagonist GVT ([d(CH$_2$)$_5$, Tyr (Me)$^2$, Orn$^8$]-Vasotocin; from Peninsula), at 20 μM, is used as a control to block responses evoked by 8 nM AVT.

6.8 Functional Antagonism of a Human MSH Receptor by dWRL in Xenopus Fibroblasts In order to demonstrate that a human MSH receptor can be inhibited by the tripeptide antagonists, Xenopus fibroblasts were transfected with a vector expressing a human MSH receptor, and cAMP response was determined with and without the tripeptide, as illustrated by FIG. 7.

Xenopus fibroblasts (Daniolos, et al., 1990, *Pigment Cell Res* 3, 38–43) were transfected with "Vector alone" (pcDNAI/NEO, Invitrogen) or with "HMelMSHR" (pcDNAI/NEO containing a human melanoma MSH receptor insert (Mountjoy et al., 1992, *Science* 257, 1248–1251; kind gift from Roger Cone). Control=no additional drugs. MSH=5 nM μM α-MSH. The dWRL concentration was 10 μM. Forskolin=100 μM forskolin (7β-desacetyl-7β-[g-(N-methylpiperazino)-butyryl; from Calbiochem).

Transfections were performed by electroporation (≈5× 10$^{-1}$ cells per 400 μL in 70% phosphate-buffered saline, pH 7.0, plus 10 μg of test cDNA) using 0.2 cm cuvettes in a BTX ECM-600 (475 V, 720 ohm, and 400 μF). 48 hr after transfection, confluent cells, plated in 12-well tissue culture plates (Falcon), were rinsed for 1 hr with 70% L-15 medium (Sigma) containing 0.5% bovine serum albumin (BSA) (Sigma), and again for 5 min with added 0.5% bovine serum albumin (BSA) (Sigma), and again for 5 min with added 0.5 mM IBMX (3-isobutyl-1-methlylxanthine; from Aldrich). Test drugs were then added with IBMX present for 45 min and intracellular cAMP extracted with 1 ml of 60% ethanol per well. cAMP from cAMP-binding protein (21; Kit from Amersham). Each bar represents the mean and SSD of three independent measurements, except Control-HMelMSHR group were n=6. *(T-test; P<0.006) for all groups except other groups baring single asterisk. **(T-test; P<0.006) for all other groups.

As shown by FIG. 7, the dWRL tripeptide significantly inhibits the formation of cAMP in cells transfected with hMel MSHR (human melanoma MSH receptor), relative to the hMel MSHR transfected cells treated with MSH alone.

6.9 Topical Efficacy for Skin Lightening

To demonstrate that pigment lightening is induced locally at the level of the skin, dWRL, was applied topically (1 mM in H$_2$O) to the skin surface of *Xenopus laevis* (FIG. 8). A lightened albino-like skin tone resulted at the place of application. These results indicate that the peptide acts transdermally and that in vivo, under the normal condition of dark adaptation, tonic coloration is mediated by endogenous melanotropin, and that removal of this influence causes the frog to assume a lightened "albino-like" state.

6.10 Systemic Efficacy for Skin Lightening

To confirm the effect of α-MSH on tonic skin tone, dark-adapted *Xenopus laevis* were injected with dWRL (40 μmol/kg) or with D-Trp-Abu-Arg-NH$_2$ (control). dWRL caused complete lightening of every frog tested (n=8) within 20 min, whereas no change was observed in the control group (n=8) (FIG. 9).

The present invention is not to be limited in scope by the specific embodiments described herein. Indeed, various modifications of the invention in addition to those described herein will become apparent to those skilled in the art from the foregoing description and accompanying data. Such modifications are intended to fall within the scope of the claims. Various publications are recited herein, the disclosures of which are incorporated by reference herein in their entireties.

We claim:

1. A peptide antagonist of α-melanocyte stimulating hormone comprising the amino acid sequence D-Trp-Arg-Leu or D-Trp-Arg-Leu-NH$_2$.

2. A peptide antagonist of α-melanocyte stimulating hormone, that is D-Trp-Arg-Leu or D-Trp-Arg-Leu-NH$_2$.

3. The peptide antagonist of α-melanocyte stimulating hormone according to claim 1 or 2 which is purified.

4. The peptide antagonist according to claim 1 which consists of no more than 8 amino acid residues.

5. The peptide antagonist according to claim 1 which consists of no more than 12 amino acid residues.

6. A pharmaceutical composition comprising (a) a peptide, said peptide comprising the amino acid sequence D-Trp-Arg-Leu or D-Trp-Arg-Leu-NH$_2$, and (b) a pharmaceutically acceptable carrier.

7. A pharmaceutical composition according to claim 6 wherein said pharmaceutically acceptable carrier is selected from the group consisting of a solution, cream or lotion suitable for topical application, a physiological salt or buffer suitable for systemic injection, a slow release carrier and a composition suitable for oral administration.

8. A pharmaceutical composition comprising (a) a tripeptide, said tripeptide being D-Trp-Arg-Leu or D-Trp-Arg-Leu-NH$_2$, and (b) a pharmaceutically acceptable carrier.

9. The pharmaceutical composition according to claim 6 in which the peptide consists of no more than 8 amino acid residues.

10. The pharmaceutical composition according to claim 6 in which the peptide consists of no more than 12 amino acid residues.

* * * * *